(12) United States Patent
Matsuoka et al.

(10) Patent No.: US 12,122,990 B2
(45) Date of Patent: Oct. 22, 2024

(54) CULTURE CONTAINER BASE MATERIAL, CULTURE CONTAINER, AND PRODUCTION METHOD OF CULTURE CONTAINER BASE MATERIAL

(71) Applicant: TOYO SEIKAN GROUP HOLDINGS, LTD., Tokyo (JP)

(72) Inventors: Yosuke Matsuoka, Kanagawa (JP); Satoshi Tanaka, Kanagawa (JP); Takahiko Totani, Kanagawa (JP); Takaharu Nishiyama, Kanagawa (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 839 days.

(21) Appl. No.: 17/087,913

(22) Filed: Nov. 3, 2020

(65) Prior Publication Data
US 2021/0115376 A1 Apr. 22, 2021

Related U.S. Application Data

(63) Continuation of application No. PCT/JP2019/017580, filed on Apr. 25, 2019.

(30) Foreign Application Priority Data

May 3, 2018 (JP) .................. 2018-088954

(51) Int. Cl.
*C12M 1/12* (2006.01)
*C12N 1/00* (2006.01)

(52) U.S. Cl.
CPC ............... *C12M 25/00* (2013.01); *C12N 1/00* (2013.01); *C12N 2513/00* (2013.01); *C12N 2533/30* (2013.01); *C12N 2535/00* (2013.01)

(58) Field of Classification Search
CPC ......... C12M 25/00; C12M 23/20; C12N 1/00; C12N 2513/00; C12N 2533/30; C12N 2535/00; C12N 5/10
See application file for complete search history.

(56) References Cited

U.S. PATENT DOCUMENTS 5,972,176 A * 10/1999 Kirk .................. C08J 7/123
427/535
2002/0110681 A1 8/2002 Amon
2010/0273260 A1 10/2010 Odane et al.
2013/0034669 A1 2/2013 Yoon et al.
2013/0230914 A1* 9/2013 Totani .................. C12M 25/14
264/447

FOREIGN PATENT DOCUMENTS

| EP | 2628789 A1 | 8/2013 |
| EP | 3263692 A1 | 1/2018 |
| JP | S57-146568 A | 9/1982 |
| JP | H03-160984 A | 7/1991 |
| JP | H06-98756 A | 4/1994 |
| JP | 2012-80836 A | 4/2012 |
| WO | 2015146560 A1 | 10/2015 |
| WO | 2016/136251 A1 | 9/2016 |
| WO | 2019021748 A1 | 1/2019 |

OTHER PUBLICATIONS

Hyun Hee Ahn et al., Cellular Behavior of Human Adipose-Derived Stem Cells on Wettable Gradient Polyethylene Surfaces, Int. J. Mol. Sci. 2014, 15, 2075-2086; doi:10.3390/ijms15022075 (Year: 2014).*
Jing Song et al., Flame treatment of low-density polyethylene: Surface chemistry across the length scales; Applied Surface Science 253 (2007) 9489-9499 (Year: 2007).*
Wise, K., 2006. Preparing spread plates protocols. Am. Soc. Microbiol. Microbe Libr. Available at: http://www.asmscience.org/content/education/protocol/protocol, 3085. (Year: 2006).*
Takehisa Matsuda et al., "Development of Surface Photochemical Modification Method for Micropatterning of Cultured Cells", Journal of Biomedical Materials Research, vol. 29, No. 6, pp. 749-756, Jan. 31, 1995 (8 pages).
International Search Report issued in corresponding International Application No. PCT/JP2019/017580 mailed Jul. 23, 2019 (5 pages).
Written Opinion of the International Searching Authority issued in corresponding International Application No. PCT/JP2019/017580 mailed Jul. 23, 2019 (5 pages).

* cited by examiner

Primary Examiner — Christopher M Babic
Assistant Examiner — Masudur Rahman
(74) Attorney, Agent, or Firm — Osha Bergman Watanabe & Burton LLP (57) ABSTRACT

Provided is a culture container base material made of a polyolefin material, capable of readily forming a culture container for culturing adherent cells. The culture container base material is for culturing the adherent cells and made of the polyolefin material. At least a part of a surface of the base material is subjected to a surface treatment, where the surface of the base material is a culture surface of the culture container, and the surface subjected to the surface treatment has a static water contact angle of greater than 80° and a receding contact angle of less than 53°.

8 Claims, 8 Drawing Sheets

FIG. 1A

STATIC WATER CONTACT ANGLE

FIG. 1B

RECEDING CONTACT ANGLE

<CORONA TREATED PE,
 STATIC WATER CONTACT ANGLE OF 88.9°>
 CULTURED BY LAMININ COATING METHOD

FIG. 4B

<CORONA TREATED PE,
 STATIC WATER CONTACT ANGLE OF 64.6°>
 CULTURED BY LAMININ COATING METHOD

FIG. 5A

<CORONA TREATED PE,
STATIC WATER CONTACT ANGLE OF 88.9°>

CULTURED BY LAMININ ADDITION METHOD

FIG. 5B

<CORONA TREATED PE,
STATIC WATER CONTACT ANGLE OF 64.6°>

CULTURED BY LAMININ ADDITION METHOD

<EXCIMER TREATED PE,
STATIC WATER CONTACT ANGLE OF 95.5°>
CULTURED BY LAMININ COATING METHOD

FIG. 7B

<EXCIMER TREATED PE,
STATIC WATER CONTACT ANGLE OF 72.4°>
CULTURED BY LAMININ COATING METHOD

FIG. 8A

<EXCIMER TREATED PE,
 STATIC WATER CONTACT ANGLE OF 95.5°>
CULTURED BY LAMININ ADDITION METHOD

FIG. 8B

<EXCIMER TREATED PE,
 STATIC WATER CONTACT ANGLE OF 72.4°>
CULTURED BY LAMININ ADDITION METHOD

CULTURE CONTAINER BASE MATERIAL, CULTURE CONTAINER, AND PRODUCTION METHOD OF CULTURE CONTAINER BASE MATERIAL

TECHNICAL FIELD

One or more embodiments of the present invention relate to a base material for forming a culture container for culturing adherent cells and a culture container formed of the base material.

BACKGROUND

In recent years, in the fields of production of pharmaceuticals, a gene therapy, regenerative medicine, an immunotherapy, and the like, it is required to efficiently culture a large quantity of cells, tissues, microorganisms, or the like under an artificial environment.

Under such a circumstance, cells and a culture liquid are filled in a culture container and a large quantity of cells are automatically cultured in a closed system.

As a base material for forming a culture container used for such mass-culture of cells, a polyolefin material having excellent gas permeability and capable of readily forming a bag-shaped culture container can be suitably used.

Further, examples of the method for culturing the adherent cells such as iPS cells include a method in which cells are cultured by allowing them to adhere to the culture surface inside the culture container and a method in which cells are cultured by allowing them to form spheres (cell aggregates) and suspending the spheres in the culture container instead of allowing the cells to adhere to the culture surface inside the culture container.

In a case where the culture container is formed by using a polyolefin material as it is, the culture surface inside the culture container becomes hydrophobic. Thus, when the adherent cells are cultured by allowing them to adhere to the culture surface inside the culture container, the adherent cells are unable to adhere to the culture surface inside the culture container, resulting in failure of culturing.

For this reason, when the culture container for culturing the adherent cells is formed by using a base material made of the polyolefin material, the base material needs to be subjected to a surface treatment to improve the wettability (hydrophilicity) of the base material surface.

Specifically, for example, there is a known method in which the culture surface is hydrophilized such that the static water contact angle on the culture surface inside the culture container becomes 60 to 80°, thereby allowing the adherent cells to adhere to the culture surface for culturing (see Patent Literature 1).

PATENT LITERATURE

Patent Literature 1: WO 2016/136251

However, when the base material made of the polyolefin material is subjected to the hydrophilization treatment such that the static water contact angle on the base material surface becomes 60 to 80°, there is difficulty in forming the culture container.

That is, despite improving adhesiveness of the base material, the base material surfaces are tightly stuck together and become hardly detachable from each other. Further, forcible separation of these surfaces causes cloudy appearance on the base material surfaces, and such a base material cannot be used for forming the container. As such, it is very difficult to form a bag-shaped culture container by using the base material subjected to the hydrophilization treatment.

SUMMARY

Thus, the present inventors have conducted intensive studies to provide a base material made of a polyolefin material which allows adherent cells to adhere thereto and enables easy formation of a culture container. As a result, the inventors have succeeded in developing a base material capable of achieving the above aims and thereby completed one or more embodiments of the present invention.

In view of the foregoing circumstances, one or more embodiments of the present invention is to provide a base material made of a polyolefin material capable of readily forming a culture container usable for culturing adherent cells, a culture container formed by using the base material, and a method for producing a culture container base material.

To achieve the above, a culture container base material of one or more embodiments of the present invention is used for culturing adherent cells and made of a polyolefin material. At least a part of a surface of the base material is subjected to a surface treatment. The surface of the base material is used as a culture surface of the culture container, and the surface subjected to the surface treatment has a static water contact angle of greater than 80° and a receding contact angle of less than 53°.

Further, the culture container of one or more embodiments of the present invention is configured in a manner such that the surface subjected to the surface treatment of the culture container base material is formed as a culture surface.

Further, a method for producing a culture container base material of one or more embodiments of the present invention, which is a method for producing a base material of a culture container used for culturing adherent cells and made of a polyolefin material, includes a hydrophilization step of applying a surface treatment to at least a part of a surface of the base material, the surface of the base material being used as a culture surface of the culture container and a modification step of modifying the base material, the hydrophilization step and the modification step being performed such that the surface subjected to the surface treatment has a static water contact angle of greater than 80° and a receding contact angle of less than 53°.

According to one or more embodiments of the present invention, it becomes possible to provide the base material made of the polyolefin material capable of readily forming the culture container usable for culturing the adherent cells, the culture container formed by using the base material, and the method for producing the culture container base material.

DETAILED DESCRIPTION OF THE EMBODIMENTS

Hereinafter, embodiments of a culture container base material, a culture container formed by using the base material, and a method for producing a culture container base material of one or more embodiments of the present invention will be described in detail. Note that one or more embodiments of the present invention are not limited to specific contents of the following embodiments and Examples described below.

A culture container base material of one or more embodiments is used for forming a culture container used for culturing adherent cells and made of a polyolefin material.

At least a part of the surface of the base material is subjected to a surface treatment and a static water contact angle on the surface subjected to the surface treatment is greater than 80° and a receding contact angle thereon is less than 53°. Then, the surface subjected to the surface treatment is used as a culture surface of the culture container when the culture container is formed.

Figure 1A:
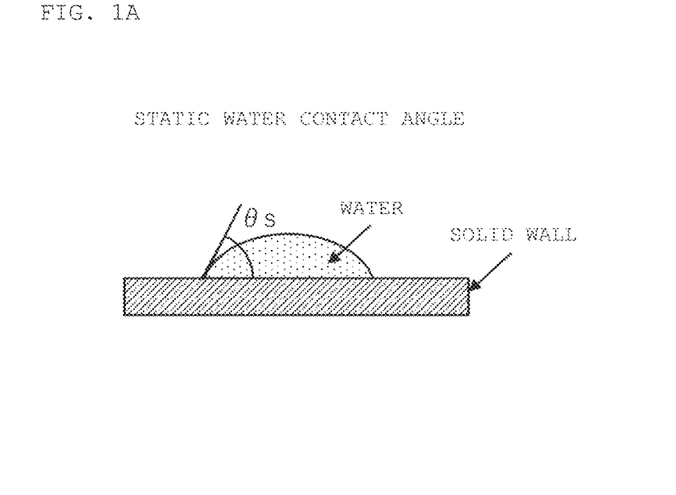
FIG. 1A is an explanatory diagram of a static water contact angle.

The static water contact angle described herein refers to an angle (θs in FIG. 1A) that is formed between the liquid surface and the solid surface at a place where the surface of the still liquid is in contact with the surface of the solid wall. There is such a relationship that when the static water contact angle is large, the hydrophobicity of the surface of the solid wall is relatively strong, while when the static water contact angle is small, the hydrophilicity of the surface of the solid wall is relatively strong.

Specifically, it is known that, when the static water contact angle on the culture surface of the culture container is from 60° to 80°, the adherent cells can suitably adhere to the culture surface for efficient culturing.

For example, the surface of the polyethylene film, one kind of polyolefin materials, has a static water contact angle of 95° or more in an untreated state, and such strong hydrophobicity does not allow the adherent cells to adhere thereto. Thus, the adherent cells cannot be cultured by the culture container formed by using the polyethylene film as it is.

Then, the surface of the polyethylene film is subjected to a surface treatment such as a corona treatment to hydrophilize the surface such that the static water contact angle on the surface becomes 60° to 80°. When the culture container having a dish shape or the like is formed by using the polyethylene film thus obtained, the adherent cells can be cultured while being adhered to the inside of the culture container.

However, the polyethylene film obtained in this manner is difficult to handle as their surfaces are tightly stuck together and hardly detachable from each other as a result of improvement in the adhesiveness, making it very difficult to use such a polyethylene film as a base material of the bag-shaped culture container.

Figure 1B:
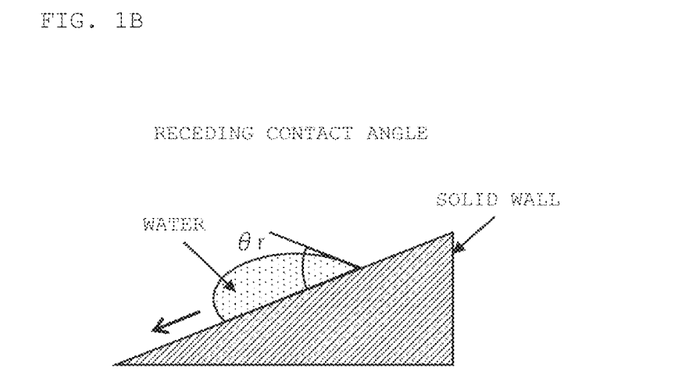
FIG. 1B is an explanatory diagram of a receding contact angle.

Further, the receding contact angle (hereinafter, also simply referred to as a receding angle) refers to a contact angle at a rear side (θr in FIG. 1B) when a water droplet slides down the surface of the solid wall. That is, it refers to a contact angle at a rear side when a water droplet, which is dropped onto the surface of the horizontally supported solid wall, starts to slide down as the solid wall is gradually inclined.

The receding angle can be used as an index for indicating dynamic wettability (hydrophilicity) of the surface of the solid wall. That is, there is such a relationship that when the receding angle is large, the hydrophobicity of the surface of the solid wall is relatively strong, while when the receding angle is small, the hydrophilicity of the surface of the solid wall is relatively strong.

The static water contact angle on the surface subjected to the surface treatment of the culture container base material of one or more embodiments is greater than 80° and the receding contact angle thereon is less than 53°.

That is, it is generally thought that this base material cannot be used for culturing adherent cells as the surface of the base material has a static water contact angle of greater than 80°, indicating strong hydrophobicity.

However, the culture container in which the culture surface is formed by the surface of this base material can actually allow the adherent cells to adhere to the culture surface for culturing.

It is considered that this is because, when the culture container base material of one or more embodiments is subjected to the hydrophilization step by the surface treatment and then to the modification step described below, while the static water contact angle indicates hydrophobicity again, the receding angle remains less than 53° indicating that the hydrophilic state is maintained.

That is, the receding angle, which reflects orientation changes of surface molecules of the solid wall in water, is considered to be a more proper index than the static water contact angle for indicating the cell adhesion to the culture surface inside the culture container filled with the culture liquid as a liquid. Specifically, the receding angle, which has a negative correlation with the number of hydrophilic groups in the interface in water, shows such a relationship that, when the receding angle is large, the hydrophobicity of the surface of the solid wall is relatively strong, while, when the receding angle is small, the hydrophilicity of the surface of the solid wall is relatively strong.

The culture container base material of one or more embodiments has a static water contact angle of greater than 80° on the surface subjected to the surface treatment and thus exhibits hydrophobicity. However, the receding angle on the treated surface is less than 53°, exhibiting hydrophilicity, thus, it is considered that the adherent cells can be adhered to the culture surface inside the culture container filled with the culture liquid.

Further, the culture container base material of one or more embodiments has a static water contact angle of greater than 80° on the treated surface, exhibiting hydrophobicity, thus their surfaces tightly stuck together can be readily detachable from each other, making it possible to readily form the culture container.

As described above, according to the culture container base material of one or more embodiments, it becomes possible to achieve both adhesion of the adherent cells to the culture container formed by using such a culture container base material and easy formation of the culture container.

As the polyolefin material for forming the culture container base material of one or more embodiments, polyethylene (PE), acyclic olefin copolymer (COC), an ethylene-vinyl acetate copolymer, an ionomer, or the like may be used, and polyethylene (PE) is particularly preferably used.

Further, the culture container is formed by using the culture container base material of one or more embodiments and the culture container thus obtained is used for culturing the adherent cells, thus the gas permeability (the oxygen permeability or the like) of the base material may be higher. For example, the density of the base material may be 0.87 g/cc or more and 0.93 g/cc or less. Further, the oxygen permeability of the base material may be 400 ml·mm/m$^2$·day·atm (37° C.-80% RH) or more.

The culture container base material of one or more embodiments may be produced by the following method.

First, at least apart of the surface of the base material made of the polyolefin material is subjected to the hydrophilization step of applying the surface treatment. The surface subjected to the surface treatment in the hydrophilization step is used as the culture surface inside the culture container when the culture container is formed.

As the surface treatment, a corona treatment, an excimer treatment, a plasma treatment, or the like may be used, and a corona treatment or an excimer treatment is particularly preferably used without being limited thereto.

Next, the modification treatment is performed in the modification step of modifying this culture container base material.

In the modification step, the culture container base material may be modified while being left still at from 45° C. to 55° C. Further, the modification step may be performed at from 43° C. to 60° C.

Further, the modification step is performed for a period from 3 days to 3 months, from 2 weeks to 3 months, or from 1 to 2 months. Note that the modification step can be performed for 3 months or more.

By performing the hydrophilization step and the modification step described above, the static water contact angle on the surface subjected to the surface treatment of the base material may be more than 80° and the receding contact angle may be less than 53°.

In this operation, the static water contact angle on the treated surface may be more than 88°, more than 89°, more than 90°, more than 91°, or more than 95°.

Further, in this operation, the receding angle on the treated surface may be less than 50°, less than 46°, less than 44°, or less than 43°.

The culture container of one or more embodiments is formed such that the surface subjected to the surface treatment of the culture container base material produced in the above method becomes the culture surface.

In this operation, the culture container of one or more embodiments can be suitably formed by heat sealing the culture container base material of the one or more embodiments. Further, the culture container of one or more embodiments may be obtained by forming multiple recesses (wells) on at least one inside surface.

The surface used as the culture surface of the culture container of one or more embodiments has a static water contact angle of greater than 80° and a receding contact angle of less than 53°.

In this configuration, the static water contact angle on the surface used as the culture surface is greater than 80°, thus the surfaces are prevented from being tightly stuck together and becoming hardly detachable from each other, making it easy to produce a container (bag).

Further, the receding contact angle on the surface used as the culture surface is less than 53°, thus the adherent cells can be properly adhered to the culture surface inside the culture container filled with the culture liquid for suitable culturing.

In one or more embodiments, as the adherent cells, for example, multipotent stem cells (iPS cells and the like), embryonic stem cells (ES cells), mesenchymal stem cells, and osteocytes, cardiac muscle cells, chondrocytes, hepatocytes, epithelium cells, pancreatic cells, endothelial cells, smooth muscle cells, renal cells, and the like differentiated therefrom can be suitably used. Further, the adherent cells of one or more embodiments include floating cells such as activated lymphocytes as long as they are adhesively cultured.

As described above, according to one or more embodiments, it becomes possible to provide the base material made of the polyolefin material capable of readily forming the culture container usable for culturing the adherent cells, the culture container formed by using the base material, and the method for producing the culture container base material.

EXAMPLES

Hereinafter, tests performed for confirming effects of a culture container base material according to one or more embodiments of the present invention and a culture container formed by using the base material will be described in detail.

[Test 1]

First, a test for confirming the static water contact angle and the receding angle on the surface subjected to the surface treatment of the culture container base material of one or more embodiments was performed.

As the culture container base material, polyethylene (PE, manufactured by UBE-MARUZEN POLYETHYLENE, UMERIT 125FN) formed into a film was prepared.

Then, a polyethylene film not subjected to the surface treatment, a polyethylene film immediately after the surface treatment, a polyethylene film subjected to the surface treatment followed by the modification treatment at 50° C. for 1 month, and a polyethylene film subjected to the surface treatment followed by the modification treatment at 50° C. for 2 months were subjected to measurement of the static water contact angle and the receding angle on their surfaces (the surfaces subjected to the surface treatment in a case where the polyethylene films were subjected to the surface treatment).

That is, the static water contact angle and the receding angle were each measured on the surface of the polyethylene film not subjected to the surface treatment (Comparative example 1), the surface of the polyethylene film immediately after the surface treatment (Reference example 1), the surface of the polyethylene film subjected to the surface treatment followed by the modification treatment at 50° C. for 1 month (Example 1), and the surface of the polyethylene film subjected to the surface treatment followed by the modification treatment at 50° C. for 2 months (Example 2).

As the surface treatment, the hydrophilic treatment step was performed using a batch type corona treatment device (manufactured by KASUGA DENKI, Inc.). In the present test, the corona treatment was performed under the following conditions: an inter-electrode distance of 5 mm, an output of 520 W, a processing speed of 50 mm/s.

The measurement of the static water contact angle and the receding angle was performed by using a solid-liquid interface analysis system DropMaster 700 (manufactured by Kyowa Interface Science, Inc.). In this operation, these contact angles were measured by dropping 3 μl of pure water on each polyethylene film.

Figure 2:
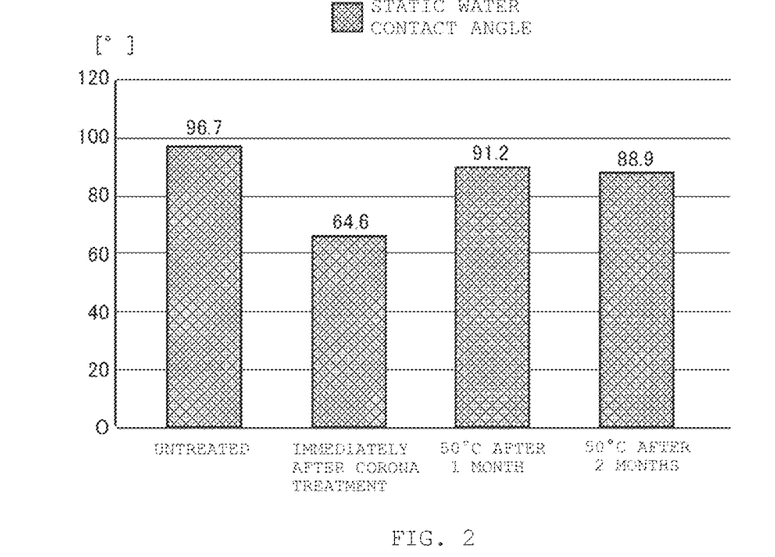
FIG. 2 is a diagram that illustrates the static water contact angle of polyethylene films (untreated, immediately after corona treatment, after modification treatment at 50° C. for 1 month, after modification treatment at 50° C. for 2 months) in Test 1.

As shown in FIG. 2, the static water contact angle on the surface of the polyethylene film not subjected to the surface treatment (Comparative example 1) was 96.7°. The polyethylene film having such a static water contact angle has strong hydrophobicity and thus does not allow adhesion of the adherent cells.

Further, the static water contact angle on the surface of the polyethylene film immediately after the surface treatment (Reference example 1) was 64.6°. Thus, this polyethylene film is hydrophilized and allows the adhesion culture of the adherent cells.

Further, the static water contact angles on the surface of the polyethylene film subjected to the surface treatment followed by the modification treatment at 50° C. for 1 month (Example 1) and the surface of the polyethylene film subjected to the surface treatment followed by the modification treatment at 50° C. for 2 months (Example 2) were 91.2° and 88.9°, respectively.

The static water contact angles of these polyethylene films were back to the numerical values close to that of the original film before the surface treatment, showing strong hydrophobicity. Thus, it can be generally considered that the adherent cells cannot be cultured by these culture container base materials.

Figure 3:
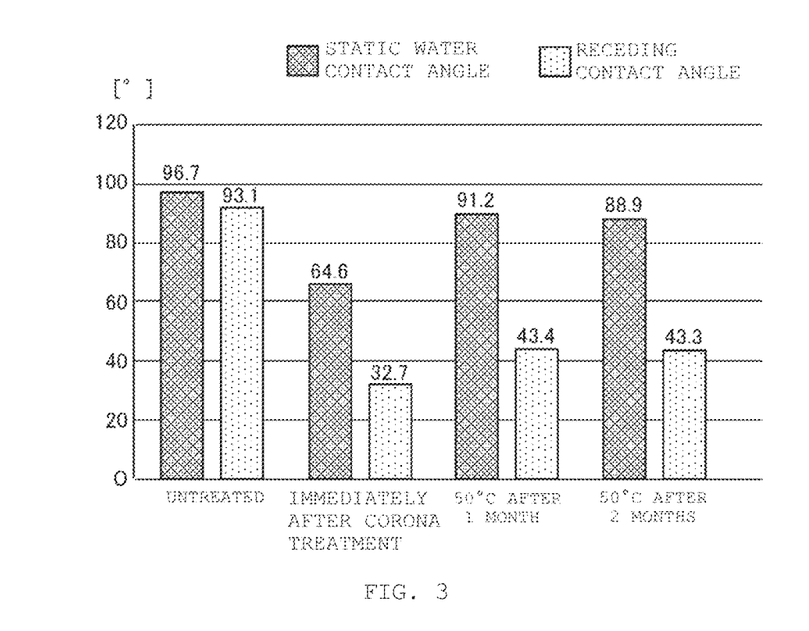
FIG. 3 is a diagram that illustrates the static water contact angle and the receding contact angle of the polyethylene films (untreated, immediately after corona treatment, after modification treatment at 50° C. for 1 month, after modification treatment at 50° C. for 2 months) in Test 1.

FIG. 3 show both the static water contact angles and the receding angles on the surface of the polyethylene film not subjected to the surface treatment (Comparative example 1), the surface of the polyethylene film immediately after the surface treatment (Reference example 1), the surface of the polyethylene film subjected to the surface treatment followed by the modification treatment at 50° C. for 1 month (Example 1), and the surface of the polyethylene film subjected to the surface treatment followed by the modification treatment at 50° C. for 2 months (Example 2).

As shown in FIG. 3, the receding angle on the surface of the polyethylene film not subjected to the surface treatment (Comparative example 1) was 93.1°. Further, the receding angle on the surface of the polyethylene film immediately after the surface treatment (Reference example 1) was 32.7°. That is, Reference example 1 shows that performing the surface treatment greatly reduces the receding angle and causes the hydrophilization of the surface.

Further, the receding angles on the surface of the polyethylene film subjected to the surface treatment followed by the modification treatment at 50° C. for 1 month (Example 1) and the surface of the polyethylene film subjected to the surface treatment followed by the modification treatment at 50° C. for 2 months (Example 2) were 43.4° and 43.3°, respectively.

That is, it is shown that, unlike the static water contact angle, the receding angle is not substantially back to the numerical value close to that of the original film before the surface treatment and remains close to that of the film immediately after the surface treatment even after the above modification step.

Further, as shown in Test 3 and Test 4 below, it is found that, according to the polyethylene film having the receding angle that indicates hydrophilicity, even if the static water contact angle indicates hydrophobicity, the adherent cells can be adhered to the culture surface inside the culture container formed by using this polyethylene film for culturing.

Further, in these polyethylene films in Example 1 and Example 2, as described above, the static water contact angle on the surface subjected to the surface treatment is back to the numerical value close to that of the original film before the surface treatment, indicating strong hydrophobicity.

Then, as shown in Test 2 below, it is found that, according to such a polyethylene film, the surfaces subjected to the surface treatment are prevented from being stuck together and becoming hardly detachable from each other, making it easy to form the culture container.

[Test 2]

Next, a test for confirming that the culture container could be readily formed by using the culture container base material of one or more embodiments was performed.

As the culture container base material, the polyethylene film subjected to the corona treatment followed by the modification treatment at 50° C. for 2 months used in Example 2 in Test 1 was used.

Then, this polyethylene film was subjected to welding using an impulse sealer to form a bag-shaped culture container.

As a result, it is found that the culture container can be readily formed without having the surfaces subjected to the surface treatment of the culture container base material being tightly stuck together or the like.

On the other hand, when the surfaces subjected to the surface treatment of the polyethylene film immediately after the surface treatment (Reference example 1) were attached together, they were tightly stuck together and became hardly detachable from each other. Further, forcible separation of these surfaces caused cloudy appearance on the polyethylene film. Thus, it is found that, according to the polyethylene film immediately after the surface treatment (without the modification treatment), it is very difficult to form a bag-shaped culture container.

[Test 3]

Next, a test for confirming that the adherent cells could be cultured by the culture container formed by using the culture container base material of one or more embodiments was performed.

Specifically, as was in Test 1, the polyethylene film subjected to the surface treatment followed by the modification treatment at 50° C. for 2 months (the static water contact angle of 88.9°, obtained in Example 2) was subjected to welding using an impulse sealer to form a dish-shaped culture container.

Further, the polyethylene film immediately after the surface treatment (the static water contact angle of 64.6°, obtained in Reference example 1) was subjected to welding using an impulse sealer to form a dish-shaped culture container.

Further, the culture surfaces of these culture containers were coated with 0.5 mg/ml laminin-511-E8 (item number 892012, manufactured by Nippi. Inc.) to 0.5 μg/cm². Then, the culture containers thus obtained were each subjected to a culture test of adherent cells (a laminin coating method).

As the adherent cells, iPS cells (strain 1231A3) were used. Further, as a medium, StemFitAK02N (item number RCAK02N, manufactured by AJINOMOTO Co., Inc.) was used.

Then, the above medium including 10 mMY-27632 (item number 253-00511, manufactured by Wako Pure Chemical Industries, Ltd.) was poured into each culture container.

Subsequently, cell suspension including the iPS cells was poured and incubation was performed at 37° C. for 7 days. In this operation, 1.5 ml of the medium and 5 μl of the cell suspension were used. The seeded cell number was about $1.3 \times 10^4$ cells. Further, the medium was replaced with a medium not containing Y-27632 at 1 day after the start of the culture, and, following then, the medium was replaced every day.

Then, the adhesion condition of the cells was observed under a microscope after 7 days of culture and adhesion of the cells was evaluated based on whether or not adhesion and extension of the cells were observed.

Figure 4A:
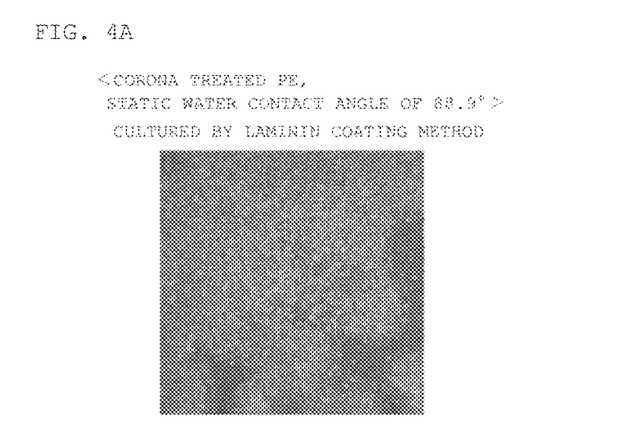
FIG. 4A is an image showing a result of a culture test (a laminin coating method, Example 2) of adherent cells using culture containers formed by using polyethylene films subjected to the corona treatment in Test 3.
Figure 4B:
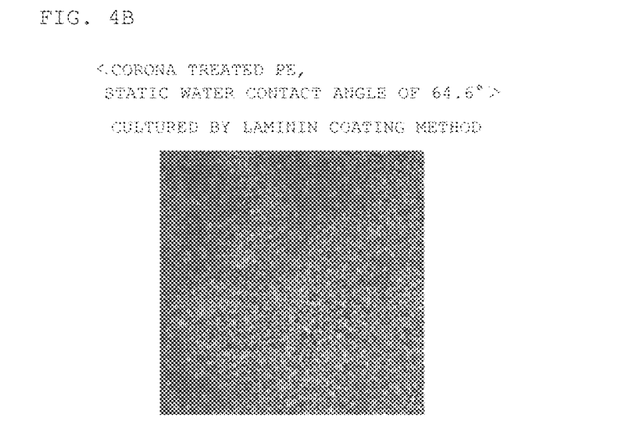
FIG. 4B is an image showing a result of a culture test (a laminin coating method, Reference Example 1) of adherent cells using culture containers formed by using polyethylene films subjected to the corona treatment in Test 3.

As a result, as shown in FIG. 4A, it is found that, according to the culture container of one or more embodiments (of which the culture surface inside the culture container has a static water contact angle of 88.9° (a value indicating hydrophobicity) and a receding angle of 43.3° (a value indicating hydrophilicity)), it is by no means inferior to the culture container having the static water contact angle indicating hydrophilicity, thus the adherent cells can be adhesively cultured.

[Test 4]

Next, a test for confirming that the adherent cells could be cultured by the culture container formed by using the culture container base material of one or more embodiments was performed by a culture method different from that in Test 3.

Specifically, as was in Test 1, the polyethylene film subjected to the surface treatment followed by the modification treatment at 50° C. for 2 months (a static water contact angle of 88.9°, obtained in Example 2) was used to form a dish-shaped culture container and the polyethylene film immediately after the surface treatment (a static water contact angle of 64.6°, obtained in Reference example 1) was used to form a dish-shaped culture container. These culture containers were subjected to a culture test of the adherent cells using a laminin addition method.

As the adherent cells, iPS cells (strain 1231A3) were used. Further, as a medium, StemFitAK02N (item number RCAK02N, manufactured by AJINOMOTO Co., Inc.) was used.

Then, the above medium including 10 mMY-27632 (item number 253-00511, manufactured by Wako Pure Chemical Industries, Ltd.) was poured into each culture container, and 0.5 mg/ml laminin-511-E8 (item number 892012, manufactured by Nippi. Inc.) was added to each culture container to 0.125 μg/cm².

Subsequently, cell suspension including the iPS cells was poured and incubation was performed at 37° C. for 7 days. In this operation, 1.5 ml of the medium and 5 μl of the cell suspension were used. The seeded cell number was about $1.3 \times 10^4$ cells. Further, the medium was replaced with a medium not containing Y-27632 at 1 day after the start of the culture, and, following then, the medium was replaced every day.

Then, the adhesion condition of the cells was observed under a microscope after 7 days of culture and adhesion of the cells was evaluated based on whether or not adhesion and extension of the cells were observed.

Figure 5A:
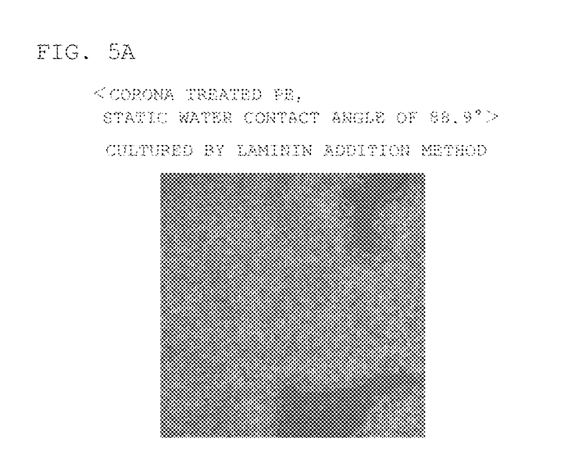
FIG. 5A is an image showing a result of a culture test (a laminin addition method, Example 2) of adherent cells using culture containers formed by using polyethylene films subjected to the corona treatment in Test 4.
Figure 5B:
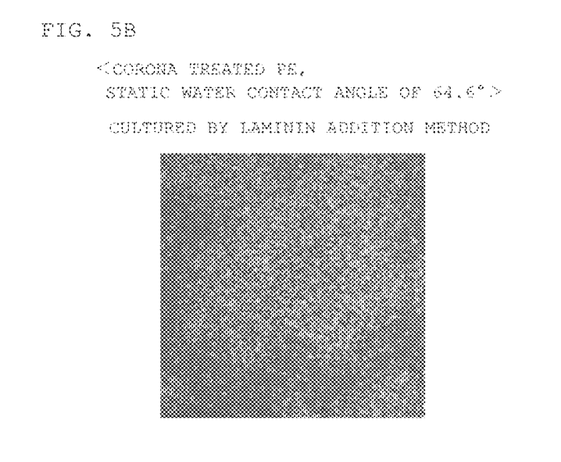
FIG. 5B is an image showing a result of a culture test (a laminin addition method, Reference Example 1) of adherent cells using culture containers formed by using polyethylene films subjected to the corona treatment in Test 4.

As a result, as shown in FIG. 5A, it is found that, according to the culture container of one or more embodiments (of which the culture surface inside the culture container has a static water contact angle of 88.9° (a value indicating hydrophobicity) and a receding angle of 43.3° (a value indicating hydrophilicity)), it is by no means inferior to the culture container having the static water contact angle indicating hydrophilicity, thus the adherent cells can be adhesively cultured.

[Test 5]

Next, a test for confirming the static water contact angle and the receding angle on the surface subjected to the excimer treatment as the surface treatment of the culture container base material of one or more embodiments was performed.

As the culture container base material, polyethylene (PE, manufactured by UBE-MARUZEN POLYETHYLENE, UMERIT 125FN) formed into a film was prepared.

Then, the polyethylene film not subjected to the surface treatment, the polyethylene film immediately after the surface treatment, the polyethylene film subjected to the surface treatment followed by the treatment at 50° C. for 1 hour, the polyethylene film subjected to the surface treatment followed by the modification treatment at 50° C. for 3 days, the polyethylene film subjected to the surface treatment followed by the modification treatment at 50° C. for 1 month, and the polyethylene film subjected to the surface treatment followed by the modification treatment at 50° C. for 2 months were subjected to measurement of the static water contact angle and the receding angle on their surfaces (the surfaces subjected to the surface treatment in a case where the polyethylene films were subjected to the surface treatment).

That is, the static water contact angle and the receding angle were each measured on the surface of the polyethylene film not subjected to the surface treatment (Comparative example 2), the surface of the polyethylene film immediately after the surface treatment (Reference example 2), the surface of the polyethylene film subjected to the surface treatment followed by the treatment at 50° C. for 1 hour (Reference example 3), the surface of the polyethylene film subjected to the surface treatment followed by the modification treatment at 50° C. for 3 days (Example 3), the surface of the polyethylene film subjected to the surface treatment followed by the modification treatment at 50° C.

for 1 month (Example 4), and the surface of the polyethylene film subjected to the surface treatment followed by the modification treatment at 50° C. for 2 months (Example 5).

As the surface treatment, the hydrophilization treatment was performed using an excimer irradiation device (manufactured by M.D.COM Inc.). In the present test, the excimer treatment was performed three times under conditions of a voltage of 12 V, an irradiation distance of 4 mm, and an irradiation speed of 2 mm/s.

The measurement of the static water contact angle and the receding angle was performed by using a solid-liquid interface analysis system DropMaster 700 (manufactured by Kyowa Interface Science, Inc.). In this operation, these contact angles were measured by dropping 3 µl of pure water on each polyethylene film.

Figure 6:
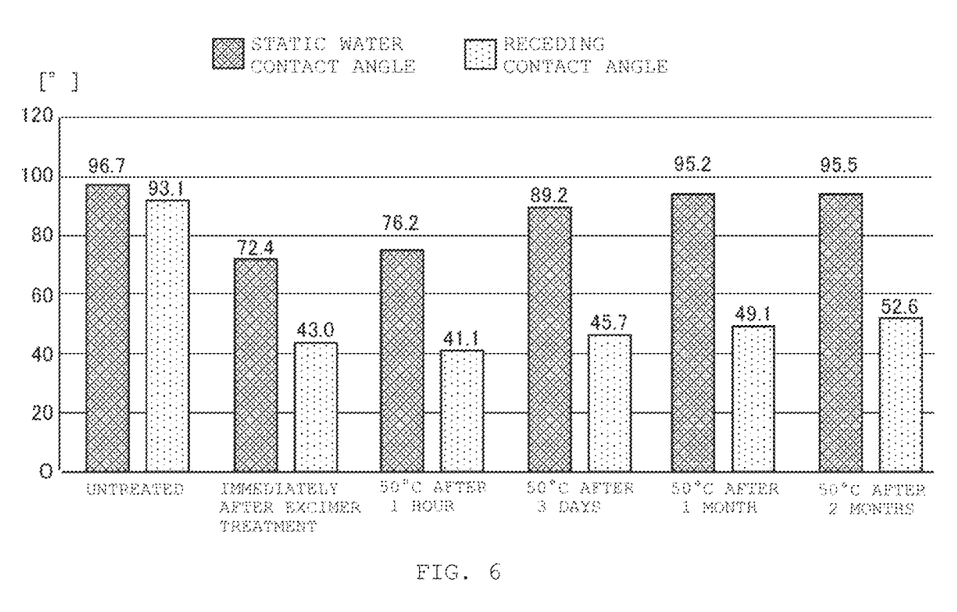
FIG. 6 is a diagram that illustrates the static water contact angle and the receding contact angle of polyethylene films (untreated, immediately after excimer treatment, after treatment at 50° C. for 1 hour, after modification treatment at 50° C. for 3 days, after modification treatment at 50° C. for 1 month, after modification treatment at 50° C. for 2 months) in Test 5.

As shown in FIG. 6, the static water contact angle and the receding angle on the surface of the polyethylene film not subjected to the surface treatment (Comparative example 2) were 96.7° and 93.1°, respectively. Further, the static water contact angle and the receding angle on the surface of the polyethylene film immediately after the surface treatment (Reference example 2) were 72.4° and 43.0°, respectively. That is, Reference example 2 shows that performing the surface treatment greatly reduces the static water contact angle and the receding angle and causes the hydrophilization of the surface. Thus, this polyethylene film is hydrophilized and can allow the adhesion culture of the adherent cells.

However, as shown in Test 6 below, according to such a polyethylene film, the surfaces subjected to the surface treatment were stuck together and became hardly detachable from each other, making it difficult to produce the culture container.

Further, the static water contact angle and the receding angle of the polyethylene film subjected to the surface treatment followed by the treatment at 50° C. for 1 hour (Reference example 3) were 76.2° and 41.1°, respectively. That is, in Reference example 3, after performing the surface treatment, the values of the static water contact angle and the receding angle indicate that the surface is hydrophilized. Thus, this polyethylene film can allow the adhesion culture of the adherent cells.

However, as shown in Test 6 below, according to such a polyethylene film, the surfaces subjected to the surface treatment were stuck together and became hardly detachable from each other, making it difficult to produce the culture container.

Further, the static water contact angle and the receding angle of the polyethylene film subjected to the surface treatment followed by the modification treatment at 50° C. for 3 days (Example 3) were 89.2° and 45.7°, respectively. That is, in Example 3, performing the surface treatment greatly reduces the receding angle, indicating that the surface is hydrophilized, although the static water contact angle has a value indicating hydrophobicity. Thus, this polyethylene film is in a hydrophilized state in the liquid and can allow the adhesion culture of the adherent cells.

Further, as shown in Test 6 below, it is found that, according to such a polyethylene film, the surfaces subjected to the surface treatment are prevented from being stuck together and becoming hardly detachable from each other, making it possible to readily produce the culture container.

Further, the static water contact angles on the surface of the polyethylene film subjected to the surface treatment followed by the modification treatment at 50° C. for 1 month (Example 4) and the surface of the polyethylene film subjected to the surface treatment followed by the modification treatment at 50° C. for 2 months (Example 5) were 95.2° and 95.5°, respectively, while their receding angles were 49.1° and 52.6°, respectively.

That is, performing the surface treatment greatly reduces the receding angle, indicating that the surface is hydrophilized, although the static water contact angle has a value indicating hydrophobicity. Thus, this polyethylene film is in a hydrophilized state in the liquid and can allow the adhesion culture of the adherent cells.

Further, according to such a polyethylene film, the surfaces subjected to the surface treatment are prevented from being stuck together and becoming hardly detachable from each other, making it possible to readily produce the culture container.

[Test 6]

Next, a test for confirming that the culture container could be readily produced by using the culture container base material of one or more embodiments was performed.

As the culture container base material, the polyethylene film subjected to the excimer treatment followed by the modification treatment at 50° C. for 2 months used in Example 5 in Test 5 was used.

Then, this polyethylene film was subjected to welding using an impulse sealer to form a bag-shaped culture container.

As a result, it is found that the culture container can be readily formed without having the surfaces subjected to the surface treatment of the culture container base material being tightly stuck together or the like.

On the other hand, when the surfaces subjected to the surface treatment of the polyethylene film immediately after the surface treatment (Reference example 2) were attached together, they were tightly stuck together and became hardly detachable from each other. Further, forcible separation of these surfaces caused cloudy appearance on the polyethylene film. Thus, it is found that, according to the polyethylene film immediately after the surface treatment, it is very difficult to form a bag-shaped culture container.

Further, when the surfaces subjected to the surface treatment of the polyethylene film subjected to the surface treatment followed by the treatment at 50° C. for 1 hour (Reference example 3) were attached together, they were tightly stuck together and became hardly detachable from each other. Further, forcible separation of these surfaces caused cloudy appearance on the polyethylene film. Thus, it is found that, according to the polyethylene film subjected to the surface treatment followed by the treatment at 50° C. for 1 hour, it is very difficult to form a bag-shaped culture container.

On the other hand, even when the surface treated surfaces of the polyethylene film subjected to the surface treatment followed by the modification treatment at 50° C. for 3 days (Example 3) were attached together, the surfaces were prevented from being tightly stuck together. Thus, it is found that, according to the polyethylene film subjected to the surface treatment followed by the modification treatment at 50° C. for 3 days or more, a bag-shaped culture container can be readily formed.

[Test 7]

Next, a test for confirming that the adherent cells could be cultured by the culture container formed by using the culture container base material of one or more embodiments was performed.

Specifically, as was in Test 5, the polyethylene film subjected to the surface treatment followed by the modification treatment at 50° C. for 2 months (a static water contact angle of 95.5°, obtained in Example 5) was subjected to welding using an impulse sealer to form a dish-shaped culture container.

Further, the polyethylene film immediately after the surface treatment (a static water contact angle of 72.4°, obtained in Reference example 2) was subjected to welding using an impulse sealer to form a dish-shaped culture container.

Further, the culture surfaces of these culture containers were coated with 0.5 mg/ml laminin-511-E8 (item number 892012, manufactured by Nippi. Inc.) to 0.5 µg/cm². Then, the culture containers thus obtained were each subjected to the culture test of the adherent cells (the laminin coating method).

As the adherent cells, iPS cells (strain 1231A3) were used. Further, as a medium, StemFitAK02N (item number RCAK02N, manufactured by AJINOMOTO Co., Inc.) was used.

Then, the above medium including 10 mMY-27632 (item number 253-00511, manufactured by Wako Pure Chemical Industries, Ltd.) was poured into each culture container.

Subsequently, cell suspension including the iPS cells was poured and incubation was performed at 37° C. for 7 days. In this operation, 1.5 ml of the medium and 5 µl of the cell suspension were used. The seeded cell number was about $1.3 \times 10^4$ cells. Further, the medium was replaced with a medium not containing Y-27632 at 1 day after the start of the culture, and, following then, the medium was replaced every day.

Then, the adhesion condition of the cells was observed under a microscope after 7 days of culture and adhesion of the cells was evaluated based on whether or not adhesion and extension of the cells were observed.

Figure 7A:
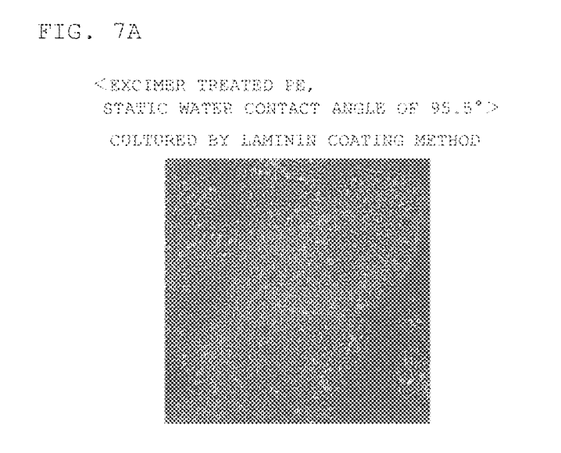
FIG. 7A is an image showing a result of the culture test (the laminin coating method, Example 5) of the adherent cells using culture containers formed by using polyethylene films subjected to the excimer treatment in Test 7.
Figure 7B:
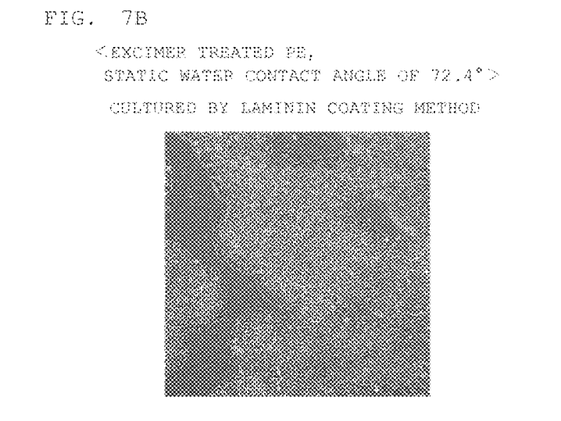
FIG. 7B is an image showing a result of the culture test (the laminin coating method, Reference Example 2) of the adherent cells using culture containers formed by using polyethylene films subjected to the excimer treatment in Test 7.

As a result, as shown in FIG. 7A, it is found that, according to the culture container of one or more embodiments (of which the culture surface inside the culture container has a static water contact angle of 95.5° (a value indicating hydrophobicity) and a receding angle of 52.6° (a value indicating hydrophilicity)), it is by no means inferior to the culture container having the static water contact angle indicating hydrophilicity, thus the adherent cells can be adhesively cultured.

[Test 8]

Next, a test for confirming that the adherent cells could be cultured by the culture container formed by using the culture container base material of one or more embodiments was performed by a culture method different from that in Test 7.

Specifically, as was in Test 5, the polyethylene film subjected to the surface treatment followed by the modification treatment at 50° C. for 2 months (a static water contact angle of 95.5°, obtained in Example 5) was used to form a dish-shaped culture container and the polyethylene film immediately after the surface treatment (a static water contact angle of 72.4°, obtained in Reference example 2) was used to form a dish-shaped culture container. These culture containers were subjected to the culture test of the adherent cells using the laminin addition method.

As the adherent cells, iPS cells (strain 1231A3) were used. Further, as a medium, StemFit AK02N (item number RCAK02N, manufactured by AJINOMOTO Co., Inc.) was used.

Then, the above medium including 10 mMY-27632 (item number 253-00511, manufactured by Wako Pure Chemical Industries, Ltd.) was poured into each culture container, and 0.5 mg/ml laminin-511-E8 (item number 892012, manufactured by Nippi. Inc.) was added to each culture container to 0.125 µg/cm².

Subsequently, cell suspension including the iPS cells was poured and incubation was performed at 37° C. for 7 days. In this operation, 1.5 ml of the medium and 5 µl of the cell suspension were used. The seeded cell number was about $1.3 \times 10^4$ cells. Further, the medium was replaced with a medium not containing Y-27632 at 1 day after the start of the culture, and, following then, the medium was replaced every day.

Then, the adhesion condition of the cells was observed under a microscope after 7 days of culture and adhesion of the cells was evaluated based on whether or not adhesion and extension of the cells were observed.

Figure 8A:
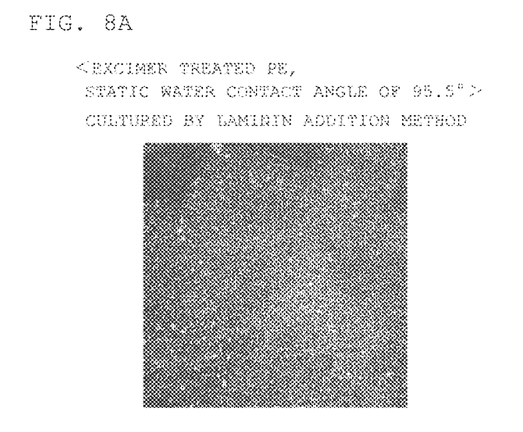
FIG. 8A is an image showing a result of the culture test (the laminin addition method, Example 5) of the adherent cells using culture containers formed by using polyethylene films subjected to the excimer treatment in Test 8.
Figure 8B:
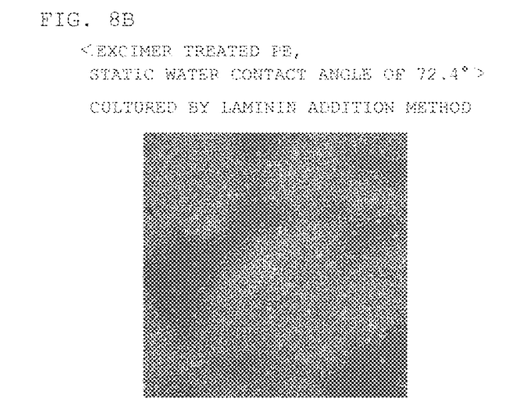
FIG. 8B is an image showing a result of the culture test (the laminin addition method, Reference Example 2) of the adherent cells using culture containers formed by using polyethylene films subjected to the excimer treatment in Test 8.

As a result, as shown in FIG. 8A, it is found that, according to the culture container of one or more embodiments (of which the culture surface inside the culture container has a static water contact angle of 95.5° (a value indicating hydrophobicity) and a receding angle of 52.6° (a value indicating hydrophilicity)), it is by no means inferior to the culture container having the static water contact angle indicating hydrophilicity, thus the adherent cells can be adhesively cultured.

As described above, it is found that, according to the culture container base material of one or more embodiments, the culture container can be readily produced. Further, it is found that, according to the culture container formed by using this culture container base material, the adherent cells can be suitably cultured.

One or more embodiments of the present invention are not limited to the above-mentioned embodiments, and it is needless to say that various modifications are possible within the scope of one or more embodiments of the present invention.

For example, in the above-mentioned Examples, the corona treatment and the excimer treatment were used as the surface treatment. However, other surface treatments may be used. Further, the iPS cells (strain 1231A3) were used as the adherent cells. However, it is possible to make appropriate modifications such as using other adherent cells.

One or more embodiments of the present invention can be suitably used for producing the culture container for culturing iPS cells and other adherent cells including activated lymphocytes.

The documents described in the specification and the Japanese patent applications claiming the priority under the Paris Convention to one or more embodiments of the invention are incorporated herein by reference in its entirety.

Although the disclosure has been described with respect to only a limited number of embodiments, those skilled in the art, having benefit of this disclosure, will appreciate that various other embodiments may be devised without departing from the scope of one or more embodiments of the present invention. Accordingly, the scope of one or more embodiments of the invention should be limited only by the attached claims.

The invention claimed is:

1. A culture container base material for culturing adherent cells comprising:
 a polyolefin material;
 a surface, wherein at least a part of the surface of the culture container base material is subjected to a surface treatment,
 wherein:
  the surface treatment comprises a hydrophilization treatment and a modification treatment,
  a static water contact angle of the at least a part of the surface of the culture container base material that is subjected to the surface treatment comprising the hydrophilization treatment and the modification treatment is greater than 80°, a receding contact angle of the at least a part of the surface of the culture container base material that is subjected to the surface treatment comprising the hydrophilization treatment and the modification treatment is less than 53°, and the modification treatment is performed at a temperature in a range of from 45° C. to 55° C.

2. The culture container base material according to claim 1, wherein the hydrophilization treatment is a corona treatment or an excimer treatment.

3. The culture container base material according to claim 1, wherein the polyolefin material is polyethylene.

4. The culture container base material according to claim 1, wherein the static water contact angle is greater than 95°.

5. The culture container base material according to claim 1, wherein the receding contact angle is less than 44°.

6. A culture container, wherein the surface subjected to the surface treatment of the culture container base material according to claim 1 is formed as the culture surface.

7. A method for producing a culture container base material for culturing adherent cells, the method comprising:

applying a surface treatment to hydrophilize at least a part of a surface of the culture container base material, wherein the surface of the culture container base material is a culture surface of a culture container; and modifying the culture container base material, wherein the applying and modifying are performed such that the surface subjected to the surface treatment has a static water contact angle of greater than 80° and a receding contact angle of less than 53°, and wherein the culture container base material comprises a polyolefin material, and the modifying is performed at a temperature ranging from 45° C. to 55° C.

8. The method for producing the culture container base material according to claim 7, wherein the modifying is performed for a period ranging from 3 days to 3 months.

* * * * *